United States Patent [19]

King et al.

[11] Patent Number: 5,102,568
[45] Date of Patent: Apr. 7, 1992

[54] THIADIAZOLE COMPOUNDS AND LUBRICANT ADDITIVES THEREOF

[75] Inventors: James P. King, Upper Gwyned; Billy L. Hill, Douglas Township, Berks County, both of Pa.

[73] Assignee: ATOCHEM North America, Inc., Philadelphia, Pa.

[21] Appl. No.: 152,682

[22] Filed: Feb. 5, 1988

Related U.S. Application Data

[63] Continuation-in-part of Ser. No. 787,577, Oct. 15, 1985, abandoned.

[51] Int. Cl.$^5$ ............... C10M 135/36; C07D 285/00
[52] U.S. Cl. .................... 252/47.5; 252/403; 548/130; 548/142; 548/127; 548/135
[58] Field of Search .............. 252/45, 47, 47.5, 48.2, 252/48.8, 56 D, 58, 403; 548/127, 130, 135, 140

[56] References Cited

U.S. PATENT DOCUMENTS

| | | | |
|---|---|---|---|
| 2,836,564 | 5/1958 | Roberts | 252/47.5 |
| 3,914,241 | 10/1975 | Elliott | 252/32.7 |
| 4,140,643 | 2/1979 | Davis | 252/47.5 |
| 4,193,882 | 3/1980 | Gemmil | 252/47.5 |
| 4,536,189 | 8/1985 | Sung | 44/56 |
| 4,584,114 | 4/1986 | Gemmil et al. | 252/47.5 |
| 4,902,804 | 2/1990 | King et al. | 548/130 |

FOREIGN PATENT DOCUMENTS

| | | |
|---|---|---|
| 0104667 | 9/1983 | European Pat. Off. . |
| 0146087 | 12/1984 | European Pat. Off. . |
| 0223916 | 6/1987 | European Pat. Off. . |
| 62-111973 | 5/1987 | Japan . |

*Primary Examiner*—Jacqueline V. Howard
*Attorney, Agent, or Firm*—Bernard Plantz

[57] ABSTRACT

Novel thiadiazole compounds of the formula $$[Z-S-Q-S]_x M$$

where: Q is a bivalent thiadiazole ring; Z is a succinate group; M is hydrogen, a metal ion selected from the Periodic Table Groups IA, IIA, IIIA, IB, IIB, IIIB, IVB, VB, and VIB, a $(MoO_2)^{+2}$ radical, or an amine salt; and X is a whole number equal to the valence of M are used as lubricant additives for providing antiwear and antioxidant properties to lubricant compositions.

29 Claims, No Drawings

THIADIAZOLE COMPOUNDS AND LUBRICANT ADDITIVES THEREOF

RELATIONSHIP TO OTHER APPLICATIONS

This application is a continuation-in-part application of our copending application U.S. Ser. No. 787,577 (filed Oct. 15, 1985), now abandoned.

BACKGROUND OF THE INVENTION

This invention relates to novel thiadiazole compounds and lubricant compositions thereof prepared from the derivatives of dimercaptothiadiazole and maleic anhydride or a halosuccinate. Lubricating compositions containing the compound, or their metal salts, provide antiwear and antioxidant properties.

Zinc dialkyldithiophosphates have been used in lubricants as antioxidant and antiwear additives for many years (CRC Handbook of Lubrication, CRC Press, Inc., 1984). However, there has been some concern regarding the presence of phosphorous-containing compounds in crankcase lubricants that may be harmful to automobile catalytic converters. It has been considered desirable to use non-phosphorous-containing additives that can provide comparable performance. The use of the derivatives of dimercaptothiadiazole, generally, in lubricants as inhibitors for corrosion and oxidation has also been long recognized (CRC Handbook of Lubrication, CRC Press, Inc., 1984). For instance, U.S. Pat. No. 4,193,882 also teaches that the reaction products of 1,3,4-thiadiazole and oleic acid inhibit metal corrosion.

According to the present invention, it has been found that the novel organosulfur compounds and their metal salts used as lubricant additives can inhibit oxidation and improve extreme pressure and antiwear characteristics of a lubricant. Zinc and molybdenum are preferred metal ions although other metals such as nickel, cobalt, iron, tin and antimony are useful.

SUMMARY OF THE INVENTION

The compound of the invention is defined as a compound of the structure

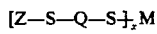

wherein:
Q is a bivalent thiadiazole ring moiety selected from the group consisting of 1,3,4-thiadiazole when M is other than hydrogen; 1,2,4-thiadiazole; 1,2,3-thiadiazole; and 1,2,5-thiadiazole;
Z is a succinate group of the structure

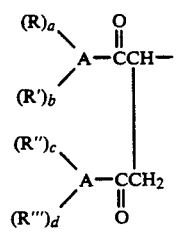

or

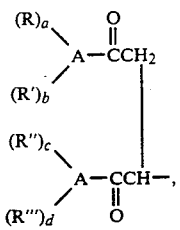

wherein
A is an oxygen or nitrogen atom, with the proviso: when A is oxygen a is 1, b is zero, c is 1, and d is zero; and when A is nitrogen a, b, c, and d are each 1;
R, R', R", and R''' are less than 31 carbons each and are independently selected from the group consisting of hydrogen, alkyl, branched or straight chain alkylene of 1 through 22 carbon atoms, arylalkyl, and heterocyclicalkenyl; with the further proviso that the number one and four carbon atoms of the succinate group Z can be linked by a single A in which case when A is oxygen a, b, c, and d are zero, and when A is nitrogen a is one and b, c, and d are zero;
M is hydrogen and x is 1 or M is a metal ion selected from the Periodic Table Groups IA, IIA, IB, IIB, IIIB, IVB, VB, VIB, IIIA, $(MoO_2)^{+2}$ radical; and amine salts; and x is a whole number equal to the valence of M. The number one and four carbon atoms of the succinate group Z are the carbons in the terminal carbonyl groups.

Preferred compounds are those as above defined wherein M is selected from the group consisting of zinc, copper with a valence state of 2, cobalt with a valence state of 2, $(MoO_2)^{+2}$ radical, aluminum, antimony with a valence state of 3, potassium, cesium, calcium, boron, tin, and molybdenum. It is more preferred that R, R', and R''' are each independently selected from the group consisting essentially of decyl, tridecyl, oleyl, 2-ethylhexyl, and isocetyl.

It is most preferred that Q is the 1,3,4-thiadiazole moiety.

Preferred specific compounds of the invention are: ditridecyl 2-(2-mercapto-1,3,4-thiadiazol-5-ylthio)-succinate; bis[ditridecyl 2-(2-thio-1,3,4-thiadiazol-5-ylthio)-succinate]-S-zinc(2+); bis[ditridecyl 2-(2-thio-1,3,4-thiadiazol-5-ylthio)-succinate]-S-dibutyltin; bis[dioleyl 2-(2-thio-1,3,4-thiadiazol-5-ylthio)-succinate]-S-molybdenum dioxide; bis[ditridecyl 2-(2-thio-1,3,4-thiadiazol-5-ylthio)-succinate]-S-molybdenum dioxide; bis[ditridecyl 2-(2-thio-1,3,4-thiadiazol-5-ylthio)-succinate]-S-cobalt(2+); bis[ditridecyl 2-(2-thio-1,3,4-thiadiazol-5-ylthio)-succinate]-S-nickel(2+); N,N'-dioleyl-2-(2-mercapto-1,3,4-thiadiazol-5-ylthio)-succinamide; bis[N,N'-dioleyl-2-(2-thio-1,3,4-thiadiazol-5-ylthio)-succinamide]-S-zinc(2+); N-oleyl-2-(2-mercapto-1,3,4-thiadiazol-5-ylthio)-succinimide; bis[N-(2-ethylhexyl)-2-(2-thio-1,3,4-thiadiazol-5-ylthio)-succinimide]-S-molybdenum dioxide; diisocetyl 2-(2-mercapto-1,3,4-thiadiazol-5-ylthio)-succinate; bis[diisocetyl 2-(2-thio-1,3,4-thiadiazol-5-ylthio)-succinate]-S-zinc(2+); bis[dihexadecyl-2(2-thio-1,3,4-thiadiazol-5-yl-thio)-succinate]-S-tributylamine; bis[dihexadecyl-2(2-thio-1,3,4-thiadiazol-5-yl-thio)-succinate]-S-copper(+2); bis[dihexadecyl-2(2-thio-1,3,4-thiadiazol-5-yl-thio)-succinate]-S-calcium(+2); bis[dihexadecyl-2(2-thio-1,3,4- thiadiazol-5-yl-thio)-succinate]-S-boron(+3); dihexadecyl-2(2-thio-1,3,4-thiadiazol-5-yl-thio)-succinate-S-potassium; dihexadecyl-2(thio-1,3,4-thiadiazol-5-yl-thio)-succinate-S-cesium.

A particularly preferred lubricant additive includes a mixture of the above compounds wherein in only a portion of the compounds A is oxygen and only one of R or R" is hydrogen.

The lubricant composition of the invention comprises a major amount of a grease or oil of lubricating viscosity and a minor amount of a compound or composition as defined above as a lubricant additive to provide enhanced properties to said grease or oil.

DETAILED DESCRIPTION OF THE INVENTION

The novel organosulfur compounds of this invention can be prepared by first reacting a 1:1 adduct of dimercaptothiadiazole and maleic anhydride with an amine or alcohol to either partially or totally convert it into an imide, amide or ester. The resulting product is then reacted with a metal salt, such as zinc oxide, zinc carbonate, zinc acetate or zinc halide, in an organic solvent at a temperature between about 50° C. and 180° C.

The extreme pressure and antiwear properties of these compounds were evaluated by means of known methods: ASTM D 2596 and ASTM D 2266, respectively. The antioxidant properties of a lubricant were obtained by a versatile thermal-oxidative method known as pressure differential scanning calorimetry (PDSC). The method measures oxidation induction time. A sample is held at an isothermal temperature in an oxidizing atmosphere. Under a set of identical conditions, the larger the oxidation induction time of a lubricant, the better is its antioxidant properties (Zeman, Stuwe and Koch, *Thermochimica Acta*, 80, 1–9, 1984, Elsevier Science Publisher B. V.).

EXAMPLE 1

Preparation of
2-(2-mercapto-1,3,4-thiadiazol-5-ylthio)-succinic anhydride

A mixture of 95 grams (0.5 moles) of 2,5-dimercapto-1,3,4-thiadiazole and 49.0 grams (0.5 moles) of maleic anhydride in 500 ml. tetrahydrofuran was refluxed for six hours. After distilling off the solvent, a light tan solid (123 g.) was obtained (m.p. 194°–196° C.). Its infrared spectrum and elemental analysis appeared to be consistent with the proposed structure.

Calculated for $C_6H_4N_2O_3S_3$: C, 29.0; H, 1.61; N, 11.3; S, 38.7. Found: C, 29.0; H, 1.64; N, 11.0; S, 38.5.

EXAMPLE 2

Preparation of ditridecyl
2-(2-mercapto-1,3,4-thiadiazol-5-ylthio)-succinate

A mixture of 99.2 grams (0.4 moles) of 2-(2-mercapto-1,3,4-thiadiazol-5-ylthio)-succinic anhydride, 160 grams (0.8 moles) of tridecyl alcohol and 0.2 grams of p-toluene sulfonic acid in 800 ml. of toluene was refluxed for 18 hours. This reaction was monitored by means of the amount of water collected in a Dean-Stark trap attached to the refluxing condenser. After distilling off the solvent, attempt was made to distill off the reaction product without success. The reaction product was a viscous oil. Its IR spectrum and elemental analysis was consistent with the proposed structure.

Calculated for $C_{33}H_{57}N_2O_4S_3$: C, 61.0; H, 9.05; N, 4.46; S, 15.3. Found: C, 60.7; H, 9.45; N, 4.40; S, 14.8.

EXAMPLE 3

Preparation of bis[ditridecyl
2(2-thio-1,3,4-thiadiazol-5-ylthio)-succinate]-S-zinc(2+)

A mixture of 6.28 grams (0.05 moles) of zinc carbonate and 31.5 grams (0.048 moles) of ditridecyl 2-(2-mercapto-1,3,4-thiadiazol-5-ylthio)-succinate in 200 ml. of toluene was refluxed for 13 hours. The reaction product was filtered to remove excess of zinc carbonate and the filtrate was subjected to distillation to remove the solvent under reduced pressures. The reaction product is an amber, viscous oil. Its IR spectrum and elemental analysis were consistent with the proposed structure. Its lubricating properties in mineral oil are recorded in Table I.

Calculated for $C_{66}H_{114}N_4C_8S_6Zn$: C, 58.0; H, 8.60; N, 4.20; S, 14.2; Zn, 4.93. Found: C, 57.5; H, 8.70; N, 2.94; S, 14.4; Zn, 5.02.

EXAMPLE 4

Preparation of bis[ditridecyl
2-(2-thio-1,3,4-thiadiazol-5-ylthio)-succinate]-S-dibutyltin A solution of 3.03 grams (0.01 mole) of dibutyl tin dichloride and 12.6 grams (0.02 moles) of ditridecyl 2-(2-mercapto-1,3,4-thiadiazol-5-ylthio)-succinate 100 ml. of hexane was refluxed for six hours. The reaction was monitored by detecting hydrogen chloride liberation. When liberation of hydrogen chloride stopped, the solvent was removed by distillation. The reaction product was an amber, viscous oil. It is soluble in mineral oil and synthetic fluids. Its lubricating properties in a paraffinic oil are listed in Table I.

Calculated for $C_{72}H_{132}N_4O_8S_6Sn$: C, 57.8; H, 8.90; N, 3.75; S, 12.9; Sn, 7.95. Found: C, 58.2, H, 9.3; N, 3.77; S, 12.1; Sn, 6.38.

EXAMPLE 5

Preparation of bis[dioleyl
2-(2-thio-1,3,4-thiadiazol-5-ylthio)-succinate]-S-molybdenum dioxide A mixture of 7.66 grams (0.01 mole) of dioleyl 2-(2-mercapto-1,3,4-thiadiazol-5-ylthio)-succinate and 0.99 grams (0.005 moles) of molybdenum dichloride dioxide in 80 ml. of toluene was refluxed for six hours. After filtering and removing the solvent from the filtrate under reduced pressures, an amber, viscous oil was obtained. The product is soluble in most non-polar solvents, mineral oils and synthetic esters. Its lubricating properties in a mineral oil and synthetic fluid are recorded in Table I.

Calculated for $C_{84}H_{144}N_4O_{10}S_6Mo$: C, 60.9; H, 8.68; N, 3.38; S, 11.6; Mo, 5.7. Found: C, 59.5; H, 9.57; N, 3.07 S, 11.4; Mo, 3.2.

EXAMPLE 6

Preparation of bis[ditridecyl
2-(2-thio-1,3,4-thiadiazol-5-ylthio)-succinate]-S-molybdenum dioxide A mixture of 7.87 grams (0.0125 moles) of ditridecyl 2-(2-mercapto-1,3,4-thiadiazol-5-ylthio)-succinate and 1.24 grams (0.00625 moles) of molybdenum dichlroide dioxide in 30 ml. of tetrahydrofuran was refluxed for three hours. The solvent was removed under reduced pressures and an amber, viscous oil was obtained. The reaction product is soluble in mineral oils and various synthetic fluid. Selected lubricating properties of this product in a mineral oil are recorded in Table I.

Calculated for $C_{64}H_{114}N_4O_8S_6Mo$: C, 55.4; H, 8.21; N, 4.0; S, 13.8. Found: C, 51.6; H, 8.37; N, 3.99; S, 13.6.

EXAMPLE 7

Preparation of bis[ditridecyl 2-(2-thio-1,3,4-thiadiazol-5-ylthio)-succinate]-S-cobalt(2+):

The title compound was prepared. The reaction product is a viscous oil. Its lubricating properties in a mineral oil are listed in Table I.

Calculated for $C_{64}H_{114}N_4O_8S_6CO$: C, 58.3; H, 8.70; N, 4.24; S, 14.6; Co, 4.4. Found: C, 58.4; H, 9.00; N, 4.79; S, 12.9; Co, 3.2.

EXAMPLE 8

Preparation of bis[ditridecyl 2-(2-thio-1,3,4-thiadiazol-5-ylthio)-succinate]-S-nickel(2+)

The title compound was prepared in the same manner as described in Example 3 by reacting ditridecyl 2-(2-mercapto-1,3,4-thiadiazol-5-ylthio)-succinate with Nickel (II) chloride in toluene. The reaction product is a viscous oil.

Calculated for $C_{64}H_{114}N_4O_8S_6Ni$: C, 58.3; H, 8.70; N, 4.24; S, 14.6. Found: C, 58.3; H, 9.04; N, 4.62; S, 12.6.

EXAMPLE 9

Preparation of N,N'-dideyl-2-(2-mercapto-1,3,4-thiadiazol-5-ylthio)-succinamide

The title compound was prepared by reacting 2-(2-mercapto-1,3,4-thiadiazol-5-ylthio)-succinic anhydride and oleylamine in 1:2 molar ratio in refluxing xylene for 14 hours. After removing the solvent, the reaction product is a brown, viscous oil and soluble in most non-polar solvents and mineral oils. Its IR spectrum and elemental analysis are consistent with the proposed structure.

Calculated for $C_{42}H_{76}N_4O_2S_3$: C, 65.9; H, 9.90; N, 7.30; S, 12.5. Found C, 65.7; H, 10.7; N, 7.22; S, 12.2.

EXAMPLE 10

Preparation of bis[N,N'-dioleyl-3-(2-thio-1,3,4-thiadiazol-5-ylthio)-succinamide]-S-zinc(2+)

The title compound was prepared by refluxing a mixture of 2-(2-mercapto-1,3,4-thiadiazol-5-ylthio)-succinic anhydride and zinc carbonate in 2:1 molar ratio in xylene for three hours. Experimental details and working up of the reaction product were similar to those described in Example 3. The reaction product is a light brown, viscous oil. Its lubricating characteristic in a mineral oil are recorded in Table I and antioxidant properties by high pressure DSC are recorded in Table II.

Calculated for $C_{84}H_{150}N_8O_4S_6Zn$: C, 63.0; H, 9.40; N, 7.03; S, 12.10. Found: C, 63.9; H, 10.1; N, 6.75; S, 10.0.

EXAMPLE 11

Preparation of N-Oleyl-2-(2-mercapto-1,3,4-thiadiazol-5-ylthio)-succinimide

A mixture of 2-(2-mercapto-1,3,4-thiadiazol-5-ylthio)-succinic anhydride and oleylamine (1:1 molar ratio) in xylene was refluxed for three hours. After removing the solvent under reduced pressure, the reaction product was a light brown, viscous oil. Both its IR spectrum and elemental analysis appeared to be consistent with the proposed structure. A sample of N-(2-ethylhexyl)-2-(2-mercapto-1,3,4-thiadiazol-5-ylthio)-succinimide was similarly prepared.

Calculated for $C_{24}H_{39}N_3O_2S_3$: C, 57.3; H, 7.70; N, 8.15. Found: C, 58.2; H, 7.96; N, 8.25.

EXAMPLE 12

Preparation of bis[N-(2-ethylhexyl)-2-(2-thio-1,3,4-thiadiazol-5-ylthio)-succinimide]-S-molybdenum dioxide A mixture of N-(2-ethylhexyl)-2-(2-mercapto-1,3,4-thiadiazol-5-ylthio)-succinimide and molybdenum dichloride dioxide in 2:1 molar ratio was refluxed in xylene for three hours. The solvent was removed by distillation under reduced pressure and the reaction product was dark green oil. The wear preventive characteristics of the reaction product in a mineral oil are listed in Table I.

Calculated for $C_{28}H_{40}N_6O_6S_6Mo$: C, 39.6; H, 4.75; S, 22.8. Found: C, 40.6; H, 4.91; S, 22.1.

EXAMPLE 13

Preparation of diisocetyl 2-(2-mercapto-1,3,4-thiadiazol-5-ylthio)-succinate

A sample of the above title compound was prepared by reacting 2-(2-mercapto-1,3,4-thiadiazol-5-ylthio)-succinic anhydride with isocetyl alcohol (1:2 molar ratio) as described in Example 2. The reaction was used for subsequent reactions with various metal salts.

EXAMPLE 14

Preparation of bis[diisocetyl 2-(2-thio-1,3,4-thiadiazol-5-ylthio)-succinate]-S-zinc(2+)

A mixture of 183 grams (0.2 moles) of diisocetyl 2-(2-mercapto-1,3,4-thiadiazol-5-ylthio)-succinate and 27.4 grams (0.125 moles) of zinc acetate dihydrate in xylene was refluxed for seven hours. The reaction mixture was filtered and the filtrate was subjected to distillation to remove solvent and other by-products. The reaction product was a viscous, brown oil and was soluble in various syntehtic fluids and mineral oils. Its lubricating properties in a paraffinic mineral oil are listed in Table I and antioxidant properties are recorded in Table II.

Calculated for $C_{76}H_{138}N_4O_8S_6Zn$: C, 61.0; H, 9.24; N, 3.75; S, 12.85. Found: C, 60.5; H, 8.95; N, 3.70; S, 13.70.

TABLE I

Lubricating Performance of Various Compositions

| Composition | Shell Four Ball EP Properties (ASTM D 2596) | | Wear Preventive Characteristics (ASTM D 2266) |
|---|---|---|---|
| | Weld Pt., kg | Load Wear Index | Scar Diam., mm[1] |
| Paraffinic Mineral Oil (P.O.)[2] | 80 | | 0.85 |
| Naphthenic Mineral Oil (N.O.)[3] | 80 | | 0.75 |
| Synthetic Ester (S.E.)[4] | 100 | | |
| 1% Zinc Complex (Example 3) in P.O. | 160–200 | 35.6 | 0.50 |
| 1% Zinc Complex (Example 3) in N.O. | 160 | | 0.48 |
| 1% Tin Complex (Example 4) in P.O. | 160 | 29.0 | 0.85 |
| 1% Mo Complex (Example 5) in P.O. | 160 | 35.0 | 0.53–0.60 |
| 1% Mo Complex (Example 5) in S.E. | 200 | | |
| 1% Zn Complex (Example 10) in P.O. | | | 0.50 |
| 1% Mo Complex (Example 12) in P.O. | | | 0.58 |
| 1% Zn Isocetyl ester (Example 14) in P.O. | 160 | 24.1 | 0.48 |
| 3% Zn Isocetyl ester (Example 14) in P.O. | 160 | 31.1 | 0.65 |

[1]167° F., 40 kg, 1200 rpm for one hour.
[2]Paraffinic straight mineral oil, 155 SUS at 100° F.
[3]Naphthenic straight mineral oil, 110 SUS at 100° F.
[4]Pentaerythrital ester.

TABLE II

Evaluation of Antioxidant Properties of Selected Compositions in Paraffinic Mineral Oil by Hight Pressure DSC Under 500 PSI Oxygen at 185° C.[1]

| Composition | Induction Time min. |
|---|---|
| Paraffinic Oil (Base Oil) | 1.90 |
| Base Oil + 1% Zn diamide (Example 10) | 72.9 |
| Base Oil + 1% ZDDP[2] | 109.0 |
| Base Oil + 1% Zn diester (Example 14) | 118.0 |

[1]Sample was placed in a Knudsen cell.
[2]Zinc diamyldithiophosphate.

EXAMPLE 15

Preparation of Potassium salt of ditridecyl 2-(3-mercapto-1,2,4-thiadiazol-5-ylthio)-succinate A solution of 10.4 g. (0.025 mole) of ditridecyl 2-chlorosuccinate in 50 ml. of absolute ethanol is added dropwise to a stirred cloudy solution of 11.3 g. (0.05 mole) of the dipotassium salt of 3,5-dimercapto-1,2,4-thiadiazole (prepared according to procedure of W. A. Thaler and J. R. McDivitt; J. Org. Chem. 36, 14–18, 1971) in 200 ml. of absolute ethanol, over a period of 10 minutes. No rise in temperature is observed. The cloudy mixture is refluxed for 18 hours.

The insoluble off white solid is filtered off, washed twice with ice cold ethanol then dried at 60° under reduced pressure to obtain 2.1 g. Calculated amount of KCL-by-product; 1.86 g. Almost completely soluble in water but insoluble in acetone.

The solvent of the filtrate is removed at 60° and reduced pressure and the yellow residue is dissolved in 100 ml. of distilled water, giving cloudy solution. The aquous solution is extracted with 4×50 ml. portions of ethyl acetate, dried with sodium sulfate and the solvent stripped off as above to obtain 18.2 g. of a yellowish brown liquid residue, which has an offensive odor similar to that of the dipotassium salt of 3,5-dimercapto-1,2,4-thiadiazole. The residue is treated with 125 ml.H₂O & 20% HCL solution to pH 1 resulting in the separation of oil. The oil is collected and dissolved in 150 ml.ether. The ether solution is washed with 3×50 ml. of distilled water, dried with sodium sulfate then heated on a steam bath to remove solvent. The liquid residue after drying at 60° C. under reduced pressure weigh 8.1 g. Again, it has offensive odor, but much less than before.

The liquid residue is treated with 200 ml. of distilled water and 10% KOH to pH 14. The alkaline mixture is extracted with 1×100 ml. of either and the ether extract is in turn washed with 50 ml. of distilled water. The ether extract is dried with sodium sulfate then heated on a steam bath to remove solvent.

The liquid residue is mixed with 300 ml. of distilled water, forming a pale yellow emulsion-like solution. The solution is heated to 55° then allowed to cool to room temperature, followed by extraction with 2×100 ml. of ether. The ether extract is dried with sodium sulfate then heated on a steam bath to remove solvent and volatiles. The residue is dried at 80° and 5–10 mm pressure to obtain a light yellowish brown liquid product.

Infrared spectrum is consistent with the proposed structure.

EXAMPLE 16

Preparation of bis[ditridecyl 2-(3-thio-1,2,4-thiodiazol-5-ylthio)-succinate]-S-Zinc (2+)

The above compound can be similarly prepared as described in Example 3 by reaction of potassium salt of ditridecyl 2-(3-mercapto-1,2,4-thiadiazol-5-ylthio)-succinate with zinc chloride in toluene.

EXAMPLE 17

Preparation of bis[dihexadecyl-2(2-thio-1,3,4-thiadiazol-5-yl-thio)succinate]-S-tributylamine A mixture of dihexadecyl-2(2-thio-1,3,4-thiadiazol-5-yl-thio-succinate and tributylamine in a 1:1 molar ratio was refluxed for 2.5 hours in xylene. The reaction product was a clear viscous oil soluble liquid.

Calculated for $C_{50}H_{97}S_3N_3O_4$: C, 65.4; 10.36; N, 4.60; S, 10.6. Found: C, 69.4; H, 10.7; N, 3.70; S, 9.97.

EXAMPLE 18

Preparation of bis[dihexadecyl-2(2-thio-1,3,4-thiadiazol-5-yl-thio)-succinate]-S-copper(+2)

A mixture of dihexadecyl-2(2-thio-1,3,4-thiadiazol-5-yl-thio)succinate and copper nitrate in a 2:1 molar ratio was refluxed in the presence of a catalyst aliquot 336 for 2 hours. The mixture was filtered. The solvent was removed from the filtrate under reduced pressure. The reaction product was an opaque viscous oil soluble liquid.

Calculated for $C_{76}H_{138}N_4S_{36}Cu$: C, 61.2; H, 9.2; N, 3.70; S, 12.9. Found: C, 63.7; H, 9.52; N, 3.65; S, 11.6.

EXAMPLE 19

Preparation of bis [dihexadecyl-2(2-thio-1,3,4-thiadiazol-5-yl-thio)-succinate]-2-calcium(+2)

A mixture of dihexadecyl-2(2-thio-1,3,4-thiadiazol-5-yl-thio)succinate and calcium oxide in a 2:1 molar ratio was refluxed in xylene for 6 hours. The mixture was filtered. Additional calcium oxide was added to the filtrate. The resulting mixture was heated for two hours. The mixture was filtered. The solvent was removed from the filtrate under reduced pressure. The reaction product was a clear viscous oil soluble liquid.

Calculated for $C_{77}H_{138}N_4S_6Ca$: C, 61.5; H, 9.3; N, 3.80; S, 13.0. Found: C, 62.0; H, 9.43; N, 3.68; S, 13.0.

EXAMPLE 20

Preparation of bis[dihexadecyl-2(2-thio-1,3,4-thiadiazol-5-yl-thio)succinate]-S-boron(+3)

A mixture of dihexadecyl-2(2-thio-1,3,4-thiadiazol-5-yl-thio)succinate and boron trichloride in 3:1 molar ratio in xylene with triethylamine was stirred in nitrogen in an ice bath for 2 hours. The mixture was filtered. The solvent was removed from the filtrate under reduce pressure. The reaction product was a semi-solid. The reaction product was partially oil soluble.

Calculated for $C_{114}H_{207}N_6S_9B$: C, 63.6; H, 9.62; N, 3.9; S, 13.4. Found: C, 62.4; H, 9.64; N, 4.06; S, 12.0.

EXAMPLE 21

Preparation of dihexadecyl-2(2-thio-1,3,4-thiadiazol-5-yl-thio)-succinate-S-potassium A mixture of 1.17 grams (0.02 moles) of potassium hydroxide and dihexadecyl-2(2-mercapto-1,3,4-thiadiazol-5-yl-thio)succinate in 200 ml of xylene was stirred for 12 hours at ambient temperature. The reaction mixture was refluxed for 3 hours. The reaction mixture was filtered. The filtrate was subjected to distillation to remove the solvent under reduced pressure. The reaction product was an amber colored liquid.

Calculated for $C_{38}H_{69}N_2S_3K$: S, 10.1. Found: S, 12.8.

EXAMPLE 22

Preparation of dihexadecyl-2(thio-1,3,4-thiadiazol-5-yl-thio)-succinate-S-cesium A mixture of 3.8 grams (0.02 moles) of cesium acetate and 14.2 grams (0.02 moles) of dihexadecyl-2(2-mercapto-1,3,4-thiadiazol-5-yl-thio)succinate in 200 ml of xylene was refluxed for three hours. The reaction mixture was filtered. The filtrate was subjected to distillation to remove the solvent under reduced pressure. The reaction product was an amber colored liquid.

Calculated for $C_{38}H_{69}N_2S_3C_3$: S, 11.3, Found: S, 8.6,

EXAMPLE 23

Two isocetyl esters of 1,3,4-thiadiazole were prepared under a set of identical conditions. The only difference is in the amounts of isocetyl alcohol used as set forth below to provide 80% esterification and 100% esterification.

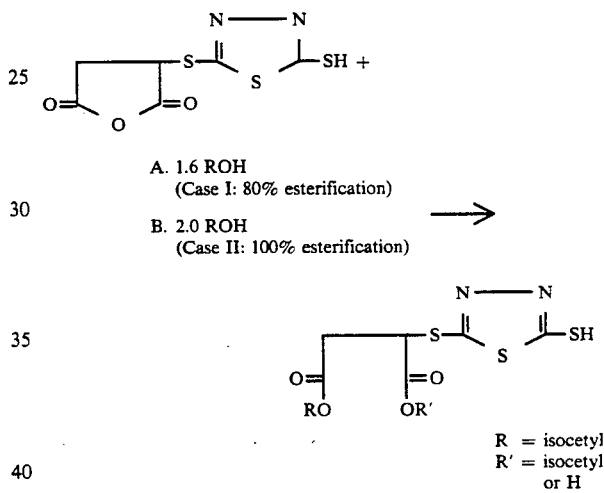

The results on antirust properties of both Case I and Case II compositions are recorded in the attached Table IV. It is clearly shown that the rust prevention properties of Case I (80% esterification) are far superior to that of Case II. The lubricating properties of Examples 17-22 are reported in Table III.

TABLE III

| | LUBRICATING PERFORMANCE OF COMPOSITIONS OF EXAMPLES 17-22 | |
|---|---|---|
| Composition | Shell Four-Ball EP Properties ASTM D 2596 Weld pt., kg | Wear Prevention Characteristics ASTM D 2266 Scar Dia., mm |
| Paraffinic Mineral Oil (P.O.)[1] | 80 | 0.85 |
| 1% amine salt (Example 17) in P.O. | 160 | 0.78 |
| 1% Cu salt (Example 18) in P.O. | 160 | 0.70 |
| 1% Ca salt (Example 19) in P.O. | 160 | 0.70 |
| 1% Boron salt (Example 20) in P.O. | 160 | 0.73 |
| 1% K salt (Example 21) in P.O. | — | 0.68 |
| 1% Cs salt (Example 22) in P.O. | — | 0.68 |

TABLE IV

Rust Prevention Properties According to ASTM D-665-83 (sea water) 80% vs. 100% Stoichiometric Alcohol Used in Ester Preparation

| Experiment No. | Description of Sample | Conc. of Additive in Mineral Oil | Observation |
|---|---|---|---|
| 6516-83 (Case I) | 80% isocetyl ester | 0.05% | 1 hr: 3% of total |

TABLE IV-continued

Rust Prevention Properties According to ASTM D-665-83 (sea water) 80% vs. 100% Stoichiometric Alcohol Used in Ester Preparation

| Experiment No. | Description of Sample | Conc. of Additive in Mineral Oil | Observation |
|---|---|---|---|
| | | | 20 hr: 5% of total area rusted |
| 6516-84 (Case II) | 100% isocetyl ester | 0.05% | 1 hr: 20% of total area rusted |
| | | | 20 hr: 70% of total area rusted |

We claim:

1. The compound of the name bis[N,N'-dioleyl-2-(2-thio-1,3,4-thiadiazol-5-ylthio)-succinamide]-S-zinc(2+).

2. The compound of the name bis[N-2-ethylhexyl)-2-(2-thio-1,3,4-thiadiazol-5-ylthio)-succinimide]-S-molybdenum dioxide.

3. The compound of the name bis[dihexadecyl-2(2-thio-1,3,4-thiadiazol-5-yl-thio)-succinate]-S-tributylamine.

4. A composition comprising a mixture of:
   (a) from 1-99 mole percent of the compound of the formula:

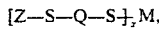

wherein:
   Q is a bivalent thiadiazole ring moiety selected from the group consisting of 1,3,4-thiadiazole when M is a metal ion selected from the Periodic Table Groups IA, IIA, IB, IIB, IIIB, IVB, VB, VIB and IIIA or a $(MoO_2)^{+2}$ radical or an amine salt; 1,2,4-thiadiazole; 1,2,3-thiadiazole; and 1,2,5-thiadiazole;
   Z is a succinate group of the structure

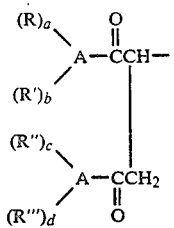

or

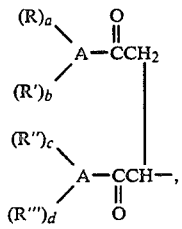

wherein
   A is an oxygen, with the proviso: when A is oxygen a is 1, b is zero, c is 1, and d is zero;
   R, R', R" and R''' are less than 31 carbons each and are independently selected from the group consisting of hydrogen, alkyl, branched or straight chain alkenyl of 1 through 22 carbon atoms, arylalkyl, and heterocyclicalkenyl; with the proviso that only one of R or R" is hydrogen and with the further proviso that the number one and four carbon atoms of the succinate group Z can be linked by a single A in which case when A is oxygen a, b, c, and d are zero;
   M is hydrogen and x is 1; M is a metal ion selected from the Periodic Table Groups IA, IIA, IB, IIB, IIIB, IVB, VB, VIB, and IIIA; M is a $(MoO_2)^{+2}$ radical; or M is an amine salt; and
   x is a whole number equal to the valence of M; and
   (b) from 99-1 mole percent of the compound of the formula:

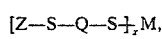

wherein:
   Q is a bivalent thiadiazole ring moiety selected from the group consisting of 1,3,4-thiadiazole when M is a metal ion selected from the Periodic Table Groups IA, IIA, IB, IIB, IIIB, IVB, VB, VIB and IIIA or a $(MoO_2)^{+2}$ radical or an amine salt; 1,2,4-thiadiazole; 1,2,3-thiadiazole; and 1,2,5-thiadiazole;
   Z is a succinate group of the structure

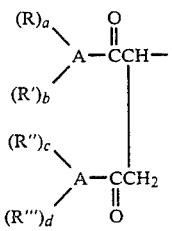

or

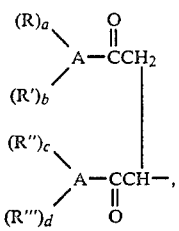

wherein
   A is an oxygen atom, with the proviso: when A is oxygen a is 1, b is zero, c is 1, and d is zero;
   R and R" are less than 31 carbon atoms each and are independently selected from the group consisting of alkyl, branched or straight chained alkenyl of 1 through 22 carbon atoms, arylalkyl and heterocyclicalkenyl;
   R' and R''' are less than 31 carbons each and are independently selected from the group consisting of hydrogen, alkyl, branched or straight chain alkenyl of 1 through 22 carbon atoms, arylalkyl, and heterocyclicalkenyl; with the further proviso that the number one and four carbon atoms of the succinate group Z can be linked by a single A in which case when A is oxygen a, b, c, and d are M is hydrogen and x is 1; M is a metal ion selected from the Periodic Table Groups IA, IIA, IB, IIB, IIIB, IVB, VB, VIB, and IIIA; M is a $(MoO_2)^{+2}$ radical; or M is an amine salt; and x is a whole number equal to the valence of M.

5. A lubricant composition comprising:
(a) a minor amount of the compound of the structure

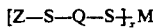

wherein:

Q is a bivalent thiadiazole ring moiety selected from the group consisting of 1,3,4-thiadiazole when M is a metal ion selected from the Periodic Table Groups IA, IIA, IIIA, IB, IIB, IIIB, IVB, VB, VIB, or a $(MoO_2)^{+2}$ radical or an amine salt; 1,2,4-thiadiazole; 1,2,3-thiadiazole; and 1,2,5-thiadiazole;

Z is a succinate group of the structure

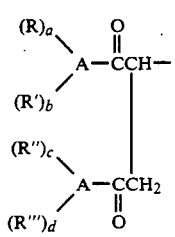

or

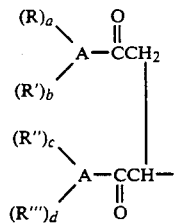

wherein

A is an oxygen or nitrogen atom, with the proviso: when a is oxygen a is 1, b is zero, c is 1, and d is zero; and when A is nitrogen a, b, c, and d are each 1;

R, R', R", and R'" are less than 31 carbons each and are independently selected from the group consisting of hydrogen, alkyl, branched or straight chain alkenyl of 1 through 22 carbon atoms, arylalkyl, and heterocyclicalkenyl; with the further proviso that the number one and four carbon atoms of the succinate group Z can be linked by a single A in which case when A is oxygen a, b, c, and d are zero, and when A is nitrogen a is one and b, c, and d are zero;

M is hydrogen and x is 1; M is a metal ion selected from the Periodic Table Groups IA, IIA, IB, IIB, IIIB, IVB, VB, VIB, and IIIA; or M is a $(MoO_2)^{+2}$ radical or M is an amine salt; and x is a whole number equal to the valence of M; and (b) a major amount of a grease or oil of lubricating viscosity.

6. The composition as defined in claim 5 wherein M is selected from the group consisting of zinc, copper with a valence state of 2, cobalt with a valence state of 2, $(MoO_2)^{+2}$ radical, aluminum, antimony with a valence state of 3, potassium, cesium, calcium, boron, tin, and molybdenum.

7. The composition as defined in claim 5 wherein R, R', R", and R'" are each independently selected from the group consisting essentially of decyl, tridecyl, oleyl, 2-ethylhexyl, and isocetyl.

8. The composition as defined in claim 5 wherein Q is the 1,3,4-thiadiazole moiety.

9. The composition as defined in claim 5 wherein the compound is bis[ditridecyl 2-(2-thio-1,3,4-thiadiazol-5-ylthio)-succinate]-S-zinc(2+).

10. The composition as defined in claim 5 wherein the compound is bis[ditridecyl 2-(2-thio-1,3,4-thiadiazol-5-ylthio)-succinate]-S-dibutyltin.

11. The composition as defined in claim 5 wherein the compound is bis[dioleyl 2-(2-thio-1,3,4-thiadiazol-5-ylthio)-succinate]-S-molybdenum dioxide.

12. The compound as defined in claim 5 wherein the compound is bis[ditridecyl 2-(2-thio-1,3,4-thiadiazol-5-ylthio)-succinate]-S-molybdenum dioxide.

13. The composition as defined in claim 5 wherein the compound is bis[ditridecyl 2-(2-thio-1,3,4-thiadiazol-5-ylthio)-succinate]-S-cobalt(2+).

14. The composition as defined in claim 5 wherein the compound is bis[ditridecyl 2-(2-thio-1,3,4-thiadiazol-5-ylthio)-succinate]-S-nickel(2+).

15. The composition as defined in claim 5 wherein the compound is bis[N,N'-dioleyl-2-(2-thio-1,3,4-thiadiazol-5-ylthio)-succinamide]-S-zinc(2+).

16. The composition as defined in claim 5 wherein the compound is bis[N-(2-ethylhexyl)-2-(2-thio-1,3,4-thiadiazol-5-ylthio)-succinimide]-S-molybdenum dioxide.

17. The compound as defined in claim 5 wherein the compound is bis[diisocetyl 2-(2-thio-1,3,4-thiadiazol-5-ylthio)-succinate]-S-zinc(2+).

18. The composition as defined in claim 5 wherein the compound is bis[dihexadecyl-2(2-thio-1,3,4-thiadiazol-5-yl-thio)-succinate]-S-tributylamine.

19. The composition as defined in claim 5 wherein the compound is bis[dihexadecyl-2(2-thio-1,3,4-thiadiazol-5-yl-thio)-succinate]-S-copper(+2).

20. The composition as defined in claim 5 wherein the compound is bis[dihexadecyl-2(2-thio-1,3,4-thiadiazol-5-yl-thio)-succinate]-S-calcium(+2).

21. The composition as defined in claim 5 wherein the compound is bis[dihexadecyl-2(2-thio-1,3,4-thiadiazol-5-yl-thio)-succinate]-S-boron(+3).

22. The composition as defined in claim 5 wherein the compound is dihexadecyl-2(2-thio-1,3,4-thiadiazol-5-yl-thio)-succinate-S-potassium.

23. The composition as defined in claim 5 wherein the compound is dihexadecyl-2(thio-1,3,4-thiadiazol-5-yl-thio)-succinate-S-cesium.

24. The composition as defined in claim 5 wherein A is oxygen and only one of R or R" is hydrogen.

25. A composition comprising:
a major amount of grease or oil of lubricating viscosity; and
a minor amount of a mixture of
(a) from 1–99 mole percent of the compound of the formula:

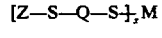

wherein:

Q is a bivalent thiadiazole ring moiety selected from the group consisting of 1,3,4-thiadiazole when M is a metal ion selected from the Periodic Table Groups IA, IIA, IB, IIB, IIIB, IVB, VB, VIB and IIIA or a $(MoO_2)^{+2}$ radical or an amine salt; 1,2,4-thiadiazole; 1,2,3-thiadiazole; and 1,2,5-thiadiazole;

Z is a succinate group of the structure

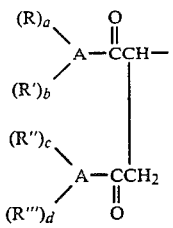

or

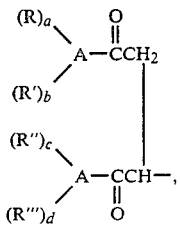

wherein

A is an oxygen, with the proviso: when A is oxygen a is 1, b is zero, c is 1, and d is zero;

R, R', R" and R''' are less than 31 carbons each and are independently selected from the group consisting of hydrogen, alkyl, branched or straight chain alkenyl of 1 through 22 carbon atoms, arylalkyl, and heterocyclicalkenyl; with the proviso that only one of R or R" is hydrogen and with the further proviso that the number one and four carbon atoms of the succinate group Z can be linked by a single A in which case when A is oxygen a, b, c, and d are zero;

M is hydrogen and x is 1; M is a metal ion selected from the Periodic Table Groups IA, IIA, IB, IIB, IIIB, IVB, VB, VIB, and IIIA; M is a $(MoO_2)^{+2}$ radical; or M is an amine salt; and x is a whole number equal to the valence of M and (b) from 99–1 mole percent of the compound of the formula:

$$[Z-S-Q-S\}_x M$$

wherein:

Q is a bivalent thiadiazole ring moiety selected from the group consisting of 1,3,4-thiadiazole when M is a metal ion selected from the Periodic Table Groups IA, IIA, IB, IIB, IIIB, IVB, VB, VIB and IIIA or a $(MoO_2)^{+2})$ radical or an amine salt; 1,2,4-thiadiazole; 1,2,3-thiadiazole; and 1,2,5-thiadiazole;

Z is a succinate group of the structure

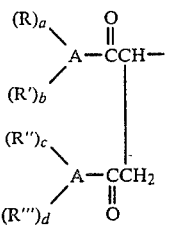

or

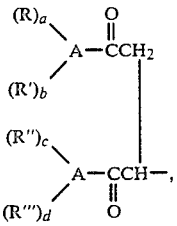

wherein

A is an oxygen atom, with the proviso: when A is oxygen a is 1, b is zero, c is 1, and d is zero;

R and R" are less than 31 carbon atoms each and are indpendently selected from the group consisting of alkyl, branched or straight chained alkenyl of 1 through 22 carbon atoms, arylalkyl and heterocyclicalkenyl;

R' and R'41 are less than 31 carbons each and are independently selected from the group consisting of hydrogen, alkyl, branched or straight chain alkenyl of 1 through 22 carbon atoms, arylalkyl, and heterocyclicalkenyl; with the further proviso that the number one and four carbon atoms of the succinate group Z can be linked by a single A in which case when A is oxygen a, b, c, and d are zero;

M is hydrogen and x is 1; M is a metal ion selected from the Periodic Table Groups IA, IIA, IB, IIB, IIIB, IVB, VB, VIB, and IIIA; M is a $(MOO_2)^{+2}$ radical; or M is an amine salt; and x is a whole number equal to the valence of M.

26. The compound ditridecyl 2-(2-mercapto-1,3,4-thiadiazol-5-ylthio)-succinate.

27. The compound N,N'-dioleyl-2-(2-mercapto-1,3,4-thiadiazol-5-ylthio)-succinamide.

28. The compound N-oleyl-2-(2-mercapto-1,3,4-thiadiazol-5-ylthio)-succinimide.

29. The compound diisocetyl 2-(2-mercapto-1,3,4-thiadiazol-5-ylthio)-succinate.

* * * * *